United States Patent [19]

Bock et al.

[11] Patent Number: 5,747,490
[45] Date of Patent: May 5, 1998

[54] ALPHA 1B ADRENERGIC RECEPTOR ANTAGONISTS

[75] Inventors: Mark G. Bock, Hatfield; Michael A. Patane, Harleysville; William C. Lumma, Pennsburg, all of Pa.

[73] Assignee: Merck & Co., Inc., Rahway, N.J.

[21] Appl. No.: 716,041

[22] Filed: Sep. 19, 1996

[51] Int. Cl.$^6$ .................. A61K 31/535; A01N 43/60; C07D 415/00; C07D 239/72
[52] U.S. Cl. .................. 514/233.8; 514/255; 514/260; 544/116; 544/291
[58] Field of Search .................. 544/116, 291; 514/233.8, 255, 260

[56] References Cited

U.S. PATENT DOCUMENTS

| | | | |
|---|---|---|---|
| 3,517,005 | 6/1970 | Cronin et al. | 260/256.4 |
| 4,287,341 | 9/1981 | Hess et al. | 544/285 |
| 4,352,928 | 10/1982 | Hiranuma et al. | 542/431 |
| 4,749,705 | 6/1988 | Tomiyama et al. | 514/259 |
| 5,064,833 | 11/1991 | Ife et al. | 514/260 |

FOREIGN PATENT DOCUMENTS

95/25726  9/1995  WIPO.

OTHER PUBLICATIONS

Phife et al., Bioorganic & Medicinal Chemistry Letters, "Marine Sponge Bis(Indole) Alkaloids That Displace Ligand Binding to a1 Adrenergic Receptors" vol. 6, No. 17, pp. 2103–2106, 1996.

Giardina et al., J. Med. Chem., "Synthesis and Biological Profile of the Enantiomers of |4-(4-Amino-6, 7-dimethoxyquinazolin-2-yl)-cis- . . . ", vol. 39, pp. 4602–4607, (1996).

Giardina et al., European Journal of Pharmacology, "Receptor binding profile of cyclazosin, a new a1B-adrenoceptor antagonist", vol. 287, pp. 13–16, (1995).

*Primary Examiner*—Mukund J. Shah
*Assistant Examiner*—Tamthom T. Ngo
*Attorney, Agent, or Firm*—Melvin Winokur; Mary A. Appollina

[57] ABSTRACT

This invention relates to certain novel compounds and derivatives thereof, their synthesis, and their use as selective alpha 1b adrenergic receptor antagonists. These compounds display submicromolar affinity for the human alpha 1b adrenergic receptor subtype while displaying at least fivefold lower affinity for the human alpha 1d and alpha 1a adrenergic receptor subtypes, and many other G-protein coupled human receptors. One application of these compounds is in the treatment of hypertension. More specifically, these compounds display selectivity for lowering blood pressure without, for example, substantially affecting urethral pressure.

17 Claims, No Drawings

1

ALPHA 1B ADRENERGIC RECEPTOR ANTAGONISTS

This application claims the benefit of U.S. Provisional Application Ser. No. 60/004,501 filed Sep. 29, 1995.

FIELD OF THE INVENTION

This invention relates to certain novel compounds and derivatives thereof, their synthesis, and their use as selective alpha 1 adrenoceptor antagonists, especially alpha 1b selective antagonists. More particularly, the compounds of the present invention are useful for treating hypertension.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Blockade of $\alpha_1$ receptors inhibits vasoconstriction induced by endogenous catecholamines; vasodilation may occur in both arteriolar resistance vessels and veins. The result is a fall in blood pressure because of decreased vascular resistance. $\alpha_2$ adrenergic receptors play an important role in regulation of the activity of the sympathetic nervous system, both peripherally and centrally. Blockade of $\alpha_2$ adrenergic receptors with selective antagonists increase sympathetic outflow and potentiate the release of norepinephrine from nerve endings, leading to activation of $\alpha_1$ and $\beta_1$ receptors in the heart and peripheral vasculature with a consequent rise in blood pressure [B. Hoffman and R. J. Lefkowitz, *Adrenergic Receptor Antagonists*, in Goodman & Gilman's *The Pharmocological Basis of Therapeutics* (8th ed., 1990)]. Thus, selective $\alpha_1$ adrenergic receptor antagonists have found use in the treatment of hypertension.

Hypertension, or high blood pressure, is a major public health concern in developed countries, it being common, asymptomatic, readily detectible and often leading to lethal complications if left untreated. Patients with hypertension die prematurely; the most common cause of death is heart disease, with stroke and renal failure also frequent. [Harrison's *Principles of Internal Medicine* (12th ed., 1991)].

Two selective $\alpha_1$ adrenergic receptor antagonists (i.e., selective for $\alpha_1$ versus $\alpha_2$ receptors) useful as antihypertensives are prazosin (i.e., 1-(4-amino-6,7-dimethoxy-2-quinazolinyl-4-(2-furanylcarbonyl)piperazine) and terazosin (i.e., 1-(4-amino-6,7-dimethoxy-2-quinazolinyl-4-(2-tetrahydrofuroyl)piperazine). In WO 92/0073, the selective ability of the R(+) enantiomer of terazosin to selectively bind to adrenergic receptors of the alpha 1 subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, is limited by their $\alpha_2$ adrenergic receptor mediated induction of increased plasma catecholamine concentration and the attendant physiological sequelae (increased heart rate and smooth muscle contraction).

For a general background on the $\alpha$-adrenergic receptors, the reader's attention is directed to Robert R. Ruffolo, Jr., $\alpha$-*Adrenoreceptors: Molecular Biology Biochemistry and Pharmacology*, (*Progress in Basic and Clinical Pharmacology* series, Karger, 1991), wherein the basis of $\alpha_1/\alpha_2$ subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting $\alpha$-adrenergic receptor affinity was explored.

The cloning, sequencing and expression of alpha receptor subtypes from animal tissues has led to the subclassification of the $\alpha_1$ receptors into $\alpha_{1a}$, (Lomasney, et al., *J. Biol. Chem.*, 266:6365–6369 (1991), rat $\alpha_{1a}$; Bruno et al., *BBRC*, 179:1485–1490 (1991), human $\alpha_{1a}$), $\alpha_{1b}$ (Cotecchia, et al., *PNAS*, 85:7159–7163 (1988), hamster $\alpha_{1b}$; Libert, et al., *Science*, (1989), dog $\alpha_{1b}$; Ramarao, et al., *J. Biol. Chem.*, 267:21936–21945 (1992), human $\alpha_{1b}$), and most recently, in a study using bovine brain, a new $\alpha_{1c}$ subtype was proposed (Schwinn, et al., *J. Biol. Chem.*, 265:8183–8189 (1990); Hirasawa et al., *BBRC* 195:902–909 (1993), described the cloning, functional expression and tissue distribution of a human $\alpha_{1c}$ adrenergic receptor; Hoehe et al., *Human Mol. Genetics* 1(5):349 (8/92) noted the existence of a two-allele PstI restriction fragment polymorphism in the $\alpha_{1c}$ adrenergic receptor gene; another study suggests that there may even be an alpha 1d receptor subtype, see Perez et al., *Mol. Pharm.*, 40:876–883, 1992). Each $\alpha_1$ receptor subtype exhibits its own pharmacologic and tissue specificities. Schwinn and coworkers noted that the cloned bovine $\alpha_{1c}$ receptor exhibited pharmacological properties proposed for the $\alpha_{1a}$ subtype. Nonetheless, based on its non-expression in tissues where the $\alpha_{1a}$ a subtype is expressed, and its sensitivity to chloroethylclonidine, the receptor was given a new designation.

The differences in the $\alpha$-adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra. Recently, it has been determined that the $\alpha_1$ adrenergic receptor that mediates human prostatic smooth muscle contraction in human prostate has the pharmacological properties of the cloned human $\alpha_{1c}$ subtype [Forray, C. et al., *Mol. Pharmacol.*, 45, 703–708 (1994)].

Effects on blood pressure, on the other hand, are mediated by binding to subtypes other than the $\alpha_{1c}$ receptor (i.e., $\alpha_{1b}$, $\alpha_{1a}$). It has now been found that compounds which selectively bind to the $\alpha_{1b}$ adrenergic receptor sybtype are effective therapeutic agents for treating cardiovascular disease conditions such as hypertension and congestive heart failure without side effects associated with non-subtype selective agents such as Prazosin or Terazosin caused by binding to the $\alpha_{1c}$ and $\alpha_{1a}$ receptor sybtypes (e.g., relaxation of urethral smooth muscle).

Typically, identification of active compounds is accomplished through use of animal tissues known to be enriched in adrenergic receptors. Thus, rat tissues have been used to screen for potential adrenergic receptor antagonists. However, because of species variability, compounds which appear active in animal tissue may not be active or sufficiently selective in humans. This results in substantial wastage of time and effort, particularly where high volume compound screening programs are employed. There is also the danger that compounds, which might be highly effective in humans, would be missed because of their absence of appreciable affinity for the heterologous animal receptors. In this regard, it has been noted that even single amino acid changes between the sequence of biologically active proteins in one species may give rise to substantial pharmacological differences. Thus, Fong et al., (*J. Biol. Chem.*, 267:25668–25671, 1992) showed that there are 22 divergent amino acid residues between the sequence of the human neurokinin-1 receptor and the homologous rat receptor. They further showed, in studies with mutant receptors, that substitution of only two amino acid residues was both necessary and sufficient to reproduce the rat receptor's antagonist binding affinity in the human receptor. Oksenberg et al., (*Nature*. 360:161–163, 1992) showed that a single amino-acid difference confers major pharmacological variation between the human and the rodent 5-hydroxytryptamine receptors. Likewise, Kuhse et al., (*Neuron*, 5:867–873, 1990) showed that a single amino-acid exchange alters the pharmacology of the neonatal rat glycine receptor subunit. This difficulty and unpredictability has resulted in a need for a compound screen which will identify compounds that will be active in humans.

These problems were solved by cloning the human adrenergic receptor subtypes (i.e., $\alpha_{1a}$, $\alpha_{1b}$ and $\alpha_{1c}$) and the use of a screening assay which enables identification of compounds which specifically interact with the desired human $\alpha_1$ adrenergic receptor subtype [PCT International Application Publication Nos. WO94/08040, published 14 Apr. 1994 and WO94/10989, published 26 May 1994]. As disclosed in the instant patent disclosure, a cloned human $\alpha_{1b}$ adrenergic receptor and a method for identifying compounds which bind the human $\alpha_{1b}$ receptor has now made possible the identification of selective human $\alpha_{1b}$ adrenergic receptor antagonists useful for treating hypertension. The instant patent disclosure describes novel compounds which selectively bind to the human $\alpha_{1b}$ receptor. These compounds are further tested for binding to other human alpha 1 receptor subtypes, as well as counterscreened against other types of receptors, thus defining the specificity of the compounds of the present invention for the human $\alpha_{1b}$ adrenergic receptor.

Because of their ability to selectively antagonize $\alpha_{1b}$ adrenergic receptors, the compounds of this invention are useful for reducing blood pressure without causing ancillary effects due to binding to the $\alpha_{1a}$ and $\alpha_{1c}$ receptor subtypes (e.g., inducing relaxation of urethral smooth muscle).

NOMENCLATURE

Recently, a new $\alpha_1$ adrenergic receptor ($\alpha_1$-AR) classification scheme similar to that proposed by Ford, et al. [*$\alpha_1$-Adrenoceptor Classification: Sharpening Occam's Razor Trends in Pharm. Sci.* 1994, 15, 167–170] was adopted at the August, 1994 meeting of the International Union of Pharmacology (IUPHAR) in Montreal, Canada. The $\alpha_1$-AR genes formerly known as $\alpha_{1a/d}$, $\alpha_{1b}$ and $\alpha_{1c}$ were renamed $\alpha_{1d}$, $\alpha_{1b}$ and $\alpha_{1a}$, respectively. This new naming system reflects the correspondence between the proteins encoded by the $\alpha_{1a}$ and $\alpha_{1b}$ genes (new IUPHAR nomenclature) and the receptors characterized by traditional pharmacological means as $\alpha_{1A}$ and $\alpha_{1B}$, respectively, in the literature. Recombinant receptors and receptors characterized pharmacologically in tissues are distinguished by lowercase and uppercase subscripts, respectively.

The above discussion contained in the Background section used the former classification scheme (i.e., $\alpha_{1a/d}$, $\alpha_{1b}$ and $\alpha_{1c}$); however, hereinafter, the new classification scheme will be utilized (i.e., $\alpha_{1d}$, $\alpha_{1b}$ and $\alpha_{1a}$). Thus, what was formerly referred to as the $\alpha_{1c}$ receptor (and $\alpha_{1c}$ receptor antagonists) will hereinafter be referred to utilizing the new nomenclature as the $\alpha_{1a}$ receptor (and $\alpha_{1a}$ receptor antagonists).

SUMMARY OF THE INVENTION

The present invention provides compounds for the treatment of hypertension. The compounds selectively antagonize the human alpha 1 adrenergic receptors. Specifically, the compounds of the present invention selectively bind to the alpha 1b adrenergic receptor at submicromolar concentrations while exhibiting at least five fold lower affinity for the alpha 1d and alpha 1a human adrenergic receptors and many other G-protein coupled receptors (e.g., serotonin). The compounds of the present invention have the structure:

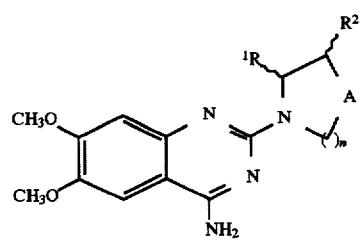

wherein

A is selected from $CR^3R^8$, N—$R^3$, O, S or $SO_2$;

$R^1$ and $R^2$ are each independently selected from hydrogen, CN, $C(O)R^4$, $CH_2OR^4$, $CH_2NR^4R^5$, $CONR^4R^5$, $CO_2R^4$ or $SO_2R^4$, provided that $R^1$ and $R^2$ are not both hydrogen;

$R^3$ is selected from hydrogen, CN, $OR^6$, $NR^6R^7$, $C(O)R^4$, $CO_2R^4$, $CONR^4R^5$, Het or $(CH_2)_mAr$ where Ar is unsubstituted, mono-, di- or tri-substituted Ar and where the substituents on Ar are independently selected from $OR^4$, $NR^4R^5$, halogen, $C_{1-8}$ alkyl, $CF_3$, nitro or CN;

$R^4$ and $R^5$ are each independently selected from hydrogen, $CH_2CF_3$, $C_{1-8}$ alkyl, $C_{3-8}$ cycloalkyl, Het or $(CH_2)_mAr$, where Ar is unsubstituted, mono-, di- or tri-substituted Ar and where the substituents on Ar are independently selected from OR⁶, halogen, NR⁶R⁷, $C_{1-8}$ alkyl, $CF_3$ or $C_{3-8}$ cycloalkyl;

$R^6$ and $R^7$ are each independently selected from hydrogen, $CH_2CF_3$, $C_{1-8}$ alkyl or $C_{3-8}$ cycloalkyl;

$R^8$ is selected from hydrogen, $C_{1-8}$ alkyl, $CF_3$, $C_{3-8}$ cycloalkyl, Het or $(CH_2)_m Ar$ where Ar is unsubstituted, mono-, di- or tri-substituted Ar and where the substituents on Ar are independently selected from OR⁴, NR⁴R⁵, halogen, $C_{1-8}$ alkyl, $CF_3$, nitro or CN;

Ar is selected from phenyl, naphthyl, furanyl, thiazolyl, pyrrolyl, thienyl, 2-, 3- or 4-pyridyl, or chromanyl;

Het is an unsubstituted, mono- or di-substituted heterocyclic ring selected from tetrahydrofuranyl, pyrrolidinyl, piperidinyl, piperazinyl or morpholinyl, where the substituents on Het are independently selected from hydroxyl, $C_{1-8}$ alkyl, $CF_3$, halogen, CN, nitro, $C_{1-4}$ alkoxy, amino or $CO_2$-$C_{1-4}$ alkyl;

m is an integer of from zero to three; and n is an integer of from one to three;

and the pharmaceutically acceptable salts thereof.

In one embodiment of the invention is the compound selected from

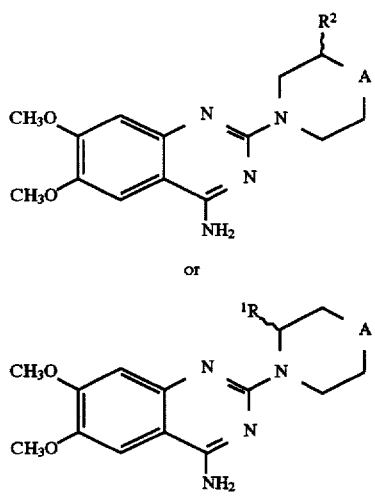

or wherein $R^1$ and $R^2$ are each independently selected from CN, C(O)R⁴, $CH_2OR^4$, $CH_2NR^4R^5$, CONR⁴R⁵, $CO_2R^4$ or $SO_2R^4$;

$R^4$ is selected from hydrogen, $CH_2CF_3$, $C_{1-6}$ alkyl, $C_{3-6}$ cycloalkyl, Het or $(CH_2)_m Ar$ where Ar is unsubstituted, mono-, di- or tri-substituted Ar and the substituents on Ar are independently selected from OR⁶, halogen, NR⁶R⁷, $C_{1-5}$ alkyl, $CF_3$ or $C_{3-8}$ cycloalkyl; and $R^5$ is selected from hydrogen, $CH_2CF_3$, $C_{1-8}$ alkyl or $C_{3-8}$ cycloalkyl; where all other variables are as defined above; and the pharmaceutically acceptable salts thereof.

In a class of the invention are the compounds wherein

A is selected from $CR^3R^8$ or N—R³;

$R^1$ and $R^2$ are each independently selected from CN, CONR⁴R⁵ or $CO_2R^4$;

$R^3$ is selected from hydrogen, C(O)R⁴ or $CO_2R^4$;

$R^4$ is selected from $C_{1-6}$ alkyl, $C_{3-6}$ cycloalkyl, tetrahydrofuranyl or $(CH_2)_m Ar$ where Ar is unsubstituted, mono-, di- or tri-substituted Ar and the substituents on Ar are independently selected from OR⁶, halogen, $C_{1-4}$ alkyl or $C_{3-8}$ cycloalkyl;

$R^5$ is selected from hydrogen, $C_{1-6}$ alkyl or $C_{3-6}$ cycloalkyl;

Ar is selected from phenyl, furanyl or chromanyl; and m is an integer of from zero to two;

where all other variables are as defined above;

and the pharmaceutically acceptable salts thereof.

In a subclass of the invention are the compound of the formula

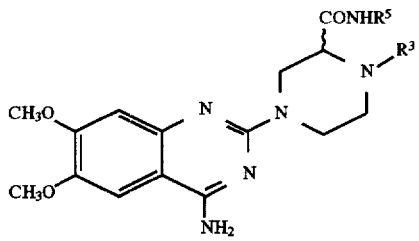

wherein $R^4$ is selected from $C_{1-4}$ alkyl, benzyl, furanyl, tetrahydrofuranyl or 4-oxo-chromene; and $R^5$ is selected from hydrogen, $C_{1-4}$ alkyl or $C_{3-6}$ cycloalkyl; and where all other variables are as defined above;

and the pharmaceutically acceptable salts thereof.

Illustrative of the invention is the compound of the formula

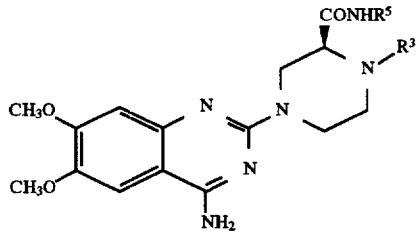

where all other variables are as defined above;

and the pharmaceutically acceptable salts thereof.

An illustration of the invention is the compound of the formula

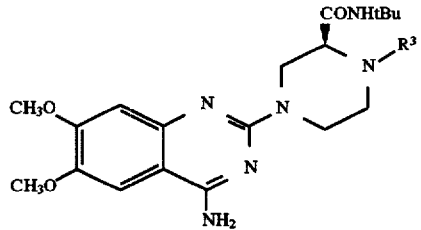

where all other variables are as defined above;

and the pharmaceutically acceptable salts thereof.

Exemplifying the invention is the compound selected from (S)-1-(4-Amino-6,7-dimethoxy-2-quinazolinyl)-4-[(benzyloxy)carbonyl]-3-(1,1-dimethylethylamino) carbonyl piperazine;

(S)-1-(4-Amino-6,7-dimethoxy-2-quinazolinyl)-3-(1,1-dimethylethylamino)carbonyl piperazine;

1-(4-amino-6,7-dimethoxy-2-quinazolinyl)-3-(1,1-dimethylethylamino)carbonyl-[(tetrahydro-2-furanyl) carbonyl]-piperazine;

(R)-1-(4-Amino-6,7-dimethoxy-2-quinazolinyl)-4-[(1,1-dimethylethoxy)carbonyl]-3-(1,1-dimethylethylamino) carbonyl piperazine;

(R)-1-(4-Amino-6,7-dimethoxy-2-quinazolinyl)-3-(1,1-dimethylethylamino)carbonyl piperazine; or 4-(4-amino-6,7-dimethoxyquinazolin-2-yl)-1-(4-oxo-4H-chromene-2-carbonyl)-piperazine-2-carboxylic acid tert-butylamide;

and the pharmaceutically acceptable salts thereof.

In a second subclass of the invention is the compound of the formula

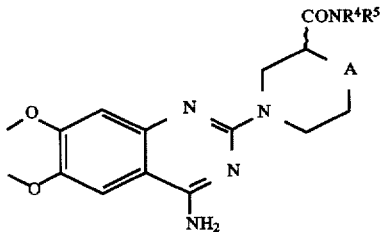

where all other variables are as defined above;
and the pharmaceutically acceptable salts thereof.

Illustrating this second subclass of the invention is the compound wherein

A is selected from $CR^3R^8$ or $N-R^3$; where all other variables are as defined above;

and the pharmaceutically acceptable salts thereof.

Exemplifying this second subclass of the invention is the compound of the formula

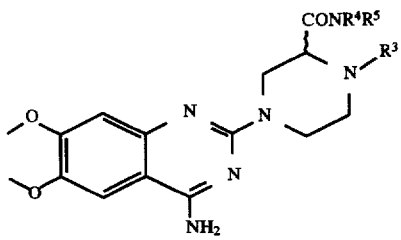

wherein $R^3$ is selected from hydrogen, $C(O)R^4$ or $CO_2R^4$;

Ar is selected from phenyl, furanyl or chromanyl; and

Het is tetrahydrofuranyl; where all other variables are as defined above;

and the pharmaceutically acceptable salts thereof.

An example of the invention is a pharmaceutical composition comprising a therapeutically effective amount of any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating hypertension in a subject in need thereof which comprises administering to the subject a therepeutically effective amount of any of the compounds or pharmaceutical compositions described above.

Further exemplifying the invention is a method of lowering blood pressure in a subject in need thereof which comprises administering to a subject in need thereof a therapeutically effective amount of any of the compounds or pharmaceutical composition described above.

More specifically illustrating the invention is a method of treating a disease which is susceptible to treatment by selective antagonism of the alpha 1b receptor which comprises administering to a subject in need thereof an amount of any of the compounds or pharmacuetical compositions described above effective to treat the disease. Diseases which are susceptible to treatment by selective antagonism of the alpha 1b receptor include, but are not limited to, hypertension, high intraocular pressure, congestive heart failure and cardiac arrhythmia.

More particularly exemplifying the invention is a method of treating hypertension in a subject in need thereof which comprises administering to the subject a therapeutically effective amount of a compound which binds to a human alpha 1b adrenergic receptor with a binding affinity greater than five-fold higher than the binding affinity with which the compound binds to a human alpha 1a adrenergic receptor, a human alpha 1d adrenergic receptor, a human alpha 2a adrenergic receptor, a human alpha 2b adrenergic receptor and a human alpha 2c adrenergic receptor. Preferably, the compound utilized in the method of treating hypertension binds to the human alpha 1b adrenergic receptor with a binding affinity at least twenty-fold higher than the binding affinity with which the compound binds to the human alpha 1a adrenergic receptor, the human alpha 1d adrenergic receptor, and the human alpha 2a, alpha 2b and alpha 2c adrenergic receptors. More preferably, the compound utilized in the method of treating hypertension binds to the human alpha 1b adrenergic receptor with a binding affinity: at least 100-fold higher than the binding affinity with which the compound binds to the human alpha 1a adrenergic receptor, at least 25-fold higher than the binding affinity with which the compound binds to the human alpha 1d adrenergic receptor, and at least 100-fold higher than the binding affinity with which the compound binds to the human alpha 2a, alpha 2b and alpha 2c adrenergic receptors. Most preferably, the compound utilized in the method of treating hypertension binds to the human alpha 1b adrenergic receptor with a binding affinity: at least 500-fold higher than the binding affinity with which the compound binds to the human alpha 1a adrenergic receptor, at least 25-fold higher than the binding affinity with which the compound binds to the human alpha 1d adrenergic receptor and at least 500-fold higher than the binding affinity with which the compound binds to the human alpha 2a, alpha 2b and alpha 2c adrenergic receptors.

More particularly illustrating the invention is the use of any of the compounds described above in the preparation of a medicament for the treatment and/or prevention of hypertension in a mammal in need thereof. Still further exemplifying the invention is the use of any of the compounds described above in the preparation of a medicament for lowering blood pressure in a mammal in need thereof.

Another example of the invention is a drug which is useful for treating and/or preventing hypertension in a mammal in need thereof, the effective ingredient of the said drug being any of the compounds described above. More specifically exemplifying the invention is a drug which is useful for lowering blood pressure in a mammal in need thereof, the effective ingredient of the said drug being any of the compounds described above.

DETAILED DESCRIPTION OF THE INVENTION

Representative compounds of the present invention exhibited high selectivity for the human alpha 1b adrenergic receptor. One implication of this selectivity is that these compounds displayed selectivity for lowering blood pressure without, for example, substantially affecting urethral pressure.

Representative compounds of this invention displayed submicromolar affinity for the human alpha 1b adrenergic receptor subtype while displaying at least five-fold lower affinity for the human alpha 1d and alpha 1a adrenergic receptor subtypes, human alpha 2a, alpha 2b and alpha 2c adrenergic receptor subtypes and many other G-protein coupled human receptors (e.g., serotonin). Particular representative compounds of this invention exhibited nanomolar affinity for the human alpha 1b adrenergic receptor subtype while displaying at least 20-fold lower affinity for the human alpha 1d and alpha 1a adrenergic receptor subtypes and the human alpha 2a, alpha 2b and alpha 2c adrenergic receptor subtypes and many other G-protein coupled human receptors (e.g., serotonin). Preferred compounds of this invention exhibited Ki's for the human alpha 1b adrenergic receptor which were more than 25-fold lower than for the human alpha 1d receptor, and more than 100-fold lower than for the human alpha 1a, alpha 2a, alpha 2b and alpha 2c adrenergic receptors, while exhibiting selectivity for the human alpha 1b adrenergic receptor over other human G-protein coupled receptors tested (e.g., serotonin). The most preferred compounds of the instant invention exhibited Ki's for the human alpha 1b adrenergic receptor which were more than 25-fold lower than for the human alpha 1d receptor and more than 500-fold lower than for the human alpha 1a, alpha 2a, alpha 2b and alpha 2c adrenergic receptors.

The compounds of the present invention are administered in dosages effective to antagonize the alpha 1b receptor where such treatment is needed, as in hypertension. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

The present invention includes within its scope prodrugs of the compounds of this invention. In general, such prodrugs will be functional derivatives of the compounds of this invention which are readily convertible in vivo into the required compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to eight total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to eight total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-8}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substituent. The term "poly-substituted" as used herein shall include di-, tri-, tetra- and penta-substitution by a named substituent.

Where multiple substituent moieties are disclosed or claimed, the substituted compound can be independently substituted by one or more of the disclosed or claimed substituent moieties, singly or plurally.

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, tetrahydrofuranyl, thiamorpholinyl, thiamorpholinyl sulfoxide, thiamorpholinyl sulfone, and oxadiazolyl. Morpholino is the same as morpholinyl.

The term "chromanyl," as used herein, refers to the group

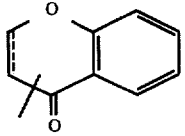

wherein the dotted line represents either a single or a double bond.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The specificity of binding of compounds showing affinity for the alpha 1b receptor is shown by comparing affinity to membranes obtained from tranfected cell lines that express the alpha 1b receptor and membranes from cell lines or tissues known to express other types of alpha (e.g., alpha 1d, alpha 1a) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1b adrenergic receptor subtype may be functionally demonstrated in anesthetized animals. These compounds may be used to decrease blood pressure without exhibiting effects on urethral pressure.

The ability of compounds of the present invention to specifically bind to the alpha 1b receptor makes them useful for the treatment of hypertension. The specificity of binding of compounds showing affinity for the alpha 1b receptor is compared against the binding affinities to other types of alpha or beta adrenergic receptors. The human alpha adrenergic receptor of the 1b subtype was recently identified, cloned and expressed as described in PCT International Application Publication Nos. WO94/08040, published 14 Apr. 1994 and WO 94/21660, published 29 Sep. 1994, each of which is hereby incorporated by reference. The cloned human alpha 1b receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting selective human alpha 1b adrenergic receptor antagonism may further be defined by counterscreening. This is accomplished according to methods known in the art using other receptors responsible for mediating diverse biological functions. [See e.g., PCT International Application Publication No. WO94/10989, published 26 May 1994; U.S. Pat. No. 5,403,847, issued Apr. 4, 1995, the contents of which are hereby incorporated by reference]. Compounds which are both selective amongst the various human alpha 1 adrenergic receptor subtypes and which have low affinity for other receptors, such as the alpha 2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha 1 adrenergic receptors. Furthermore, functional biological tests are used to confirm the effects of identified compounds as alpha 1b adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1b adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1b antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1b adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. An effective amount of the drug is ordinarily supplied at a dosage level of from about 0.0002 mg/kg to about 250 mg/kg of body weight per day. Preferably, the range is from about 0.001 to 100 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1b adrenergic receptor while minimizing any potential toxicity. In addition, co-administration or sequential administration of other agents which alleviate the effects of hypetension (e.g., $\beta$-adrenergic blocking agent, diuretic, ACE inhibitor) is desirable. Thus, in one embodiment, this includes administration of compounds of this invention and a thiazide diuretic.

The dosages of the alpha 1b adrenergic receptor and diuretic (or $\beta$ blocker) are adjusted when combined to achieve desired effects. As those skilled in the art will appreciate, dosages of the diuretic (or $\beta$ blocker) and the alpha 1b adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Abbreviations used in the instant specification, particularly the Schemes and Examples, are as follows:

Bn=benzyl
Boc or BOC=t-butyloxycarbonyl
BOPCl=bis(2-oxo-3-oxazolidinyl)phosphinic chloride
Cbz or CBZ=benzyloxycarbonyl
Cbz-Cl=benzyloxycarbonyl chloride
DAST=diethylaminosulfurtrifluoride
DEAD=diethylazodicarboxylate
DMF=N,N-dimethylformamide
EDCI=1-(3-dimethylaminopropyl)-3-ethylcarbodimide hydrochloride
Et=ethyl
$Et_3N$=triethylamine
EtOAc=ethyl acetate
EtOH=ethanol
FABHRMS=fast atom bombardment high resolution mass spectroscopy
FABLRMS=fast atom bombardment low resolution mass spectroscopy
HPLC=high performance liquid chromatography
HOAc=acetic acid
HOBt or HBT=1-hydroxy benzotriazole hydrate
iPr=isopropyl
i-PrOH or IPA=2-propanol
i-$Pr_2$NEt=diisopropylethylamine
Me=methyl
MeOH=methanol
NMR=nuclear magnetic resonance
PCTLC=preparative centrifugal thin layer chromatography
Ph=phenyl
RT=retention time
SGC=silica gel chromatography
tBu=tert-butyl
TFA=trifluoroacetic acid
THF=tetrahydrofuran
TLC=thin layer chromatography The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

The commercially available 4-amino-2-chloro-6,7-dimethoxyquinazoline, 1, allowed ready access to a variety of substituted cyclic amino derivatives 2–4. Typically thermolysis in a sealed tube at 90° C. for 12–24 hours provided analogs 2 in good to excellent yield. In the case where the amino nucleophile was a piperazine (C≡N) bearing a protecting group such as CBZ, 2a, hydrogenation was facile under standard conditions providing 3a. The synthesis of the corresponding enantiomer was achieved from the unprotected piperazine where the regiochemistry of addition was easily dictated by electronic and steric factors of the 2-(R) —CONHtBu group. The resulting deprotected piperazine 3a was further elaborated via standard acylation protocols, either EDCI mediated coupling with carboxylic acids 4b or treatment with the appropriate acid chlorides 4a.

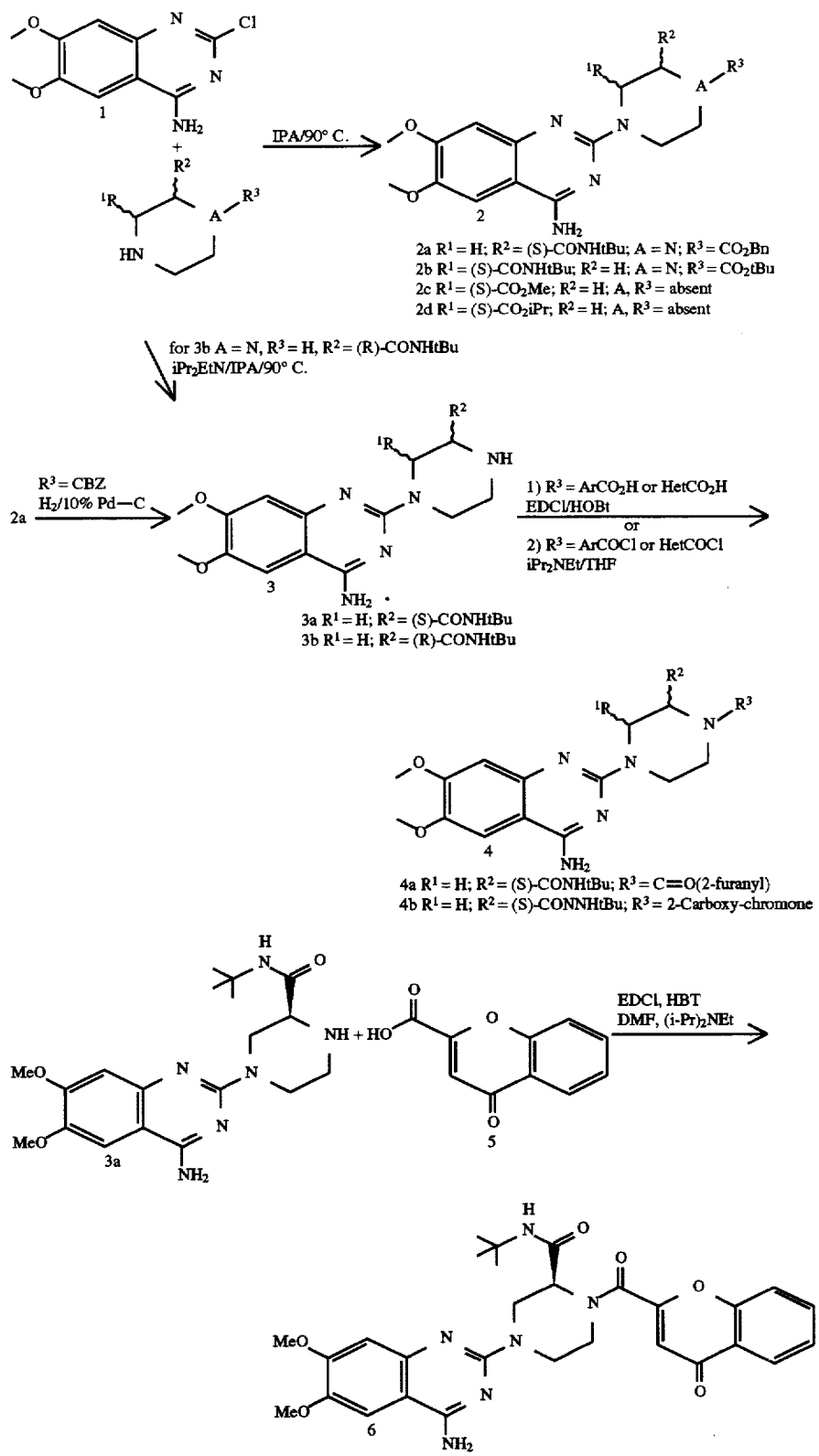
Receptor binding data for representative compounds of the present invention in cloned human receptors is shown below in Table 1.

TABLE 1

| Compound | 1a | 1b | 1d | 2a | 2b | 2c |
|---|---|---|---|---|---|---|
| alpha adrenergic receptor subtype binding (nM) | | | | | | |
| 2a | 463 | 1.0 | 29 | 683 | >10,000 | 715 |
| 3a | 1193 | 2.7 | 111 | 1172 | >10,000 | 736 |
| 4a | >3675 | 3.4 | 97 | 65% @ 10 uM | 23% @ 10 uM | 71% @ 10 uM |
|   |   |   |   | 23% @ 1 uM | 16% @ 1 uM | 42% @ 1 uM |

The following examples are provided to further define the invention without, however, limiting the invention to the particulars of these examples.

EXAMPLE 1

(S)-1-(4-Amino-6,7-dimethoxy-2-quinazolinyl)-4-[(benzyloxy)carbonyl]-3-(1,1-dimethylethylamino) carbonyl piperazine A solution of 4-amino-2-chloro-6,7-dimethoxyquinazoline (0.78 g, 3.2535 mmol) and (S)-4-[(benzyloxy)carbonyl]-3-(1,1-dimethylethylamino) carbonyl piperazine (see Askin, D. et al., Tetrahedron Letters 1994, 35, 673–676) (1.04 g, 3.2535 mmol) in 2-propanol (6 mL) was heated at 90° C. (24 h). The solvent was removed in vacuo and the residue subjected to SGC ($SiO_2$, 40 mm×240 mm, 0–10% $MeOH/CH_2Cl_2$) which afforded (S)-1-(4-Amino-6,7-dimethoxy-2-quinazolinyl)-4-[(benzyloxy) carbonyl]-3-(1,1-dimethylethylamino)carbonyl piperazine.

$^1$H NMR ($CDCl_3$, 400 MHz) for the major conformer (9:1) δ 7.30–7.40 (br m, 5H), 6.87 (br s, 2H), 6.39 (br s, 1H), 5.48 (br s, 2H), 5.20 (m, 2H), 5.18 (br d, 1H, J=13 Hz), 4.71 (br s, 1H), 4.54 (d, 1H, J=11.7 Hz), 4.10 (br s, 1H), 3.96 (s, 3H), 3.92 (s, 3H), 3.31 (br d, 1H, J=13 Hz), 3.10–3.25 (br m, 2H), 1.21 (s, 9H).

FABHRMS 523.2860 ($M^+$+H, $C_{27}H_{34}N_6O_5$ requires 523.2669)

HPLC (Vydac; C18; diameter=4.6 mm; length=15 cm; gradient=$CH_3CN$ [0.1% TFA]-$H_2O$ [0.1% TFA], 5%–95%, 95–5% over 20 min. 1.5 ml/min flow rate; RT=8.77 min; focus=214 nm; 100% pure.

Anal. Calcd for $C_{27}H_{34}N_6O_5$ and 0.1 $H_2O$ and 0.25 $CH_2Cl_2$: C=59.98, H=6.41, N=15.40. Found: C=59.95, H=6.43, N=15.01.

EXAMPLE 2

(S)-1-(4-Amino-6,7-dimethoxy-2-quinazolinyl)-3-(1,1-dimethylethylamino)carbonyl piperazine A solution of (S)-1-(4-Amino-6,7-dimethoxy-2-quinazolinyl)-4-[(benzyloxy)carbonyl]-3-(1,1-dimethylethylamino)carbonyl piperazine (1.11 g, 2.124 mmol) and 10% Pd-C (111 mg, 10 weight %) in dry EtOH (8 mL) was evacuated under high vacuum and purged to a $H_2$ balloon (14 h). The mixture was filtered through Celite (30 mm×30 mm), the filter cake washed with EtOH and concentrated in vacuo. PCTLC ($SiO_2$, 4 mm, 0–10% $CH_3OH/CH_2Cl_2$) provided the title compound.

$^1$H NMR ($CDCl_3$, 300 MHz) for the major conformer (9:1) δ 7.03 (br s, 1H), 6.87–6.96 (br m, 2H), 5.84 (br s, 2H), 5.30 (s, 1H), 4.68 (br dd, 1H), 4.43 (br d, 1H), 3.97 (s, 3H), 3.95 (s, 3H), 3.35 (dd, 1H, J=3.4, 9.1 Hz), 3.10–3.30 (br m, 2H), 3.02 (m, 1H), 2.95 (m, 1H), 1.36 (s, 9H).

FABHRMS 389.2366 ($M^+$+H, $C_{19}H_{28}N_6O_3$ requires 389.2300949)

HPLC (Vydac; C18; diameter=4.6 mm; length=15 cm; gradient=$CH_3CN$ [0.1% TFA]- $H_2O$ [0.1% TFA], 5%–95%, 95–5% over 20 min. 1.5 ml/min flow rate; RT=4.73 min; focus=214 nm; 100% pure.

Anal. Calcd for $C_{19}H_{28}N_6O_3$ and 0.3 $CH_2Cl_2$: C=55.99, H=6.96, N=20.30. Found: C=56.07, H=6.96, N=19.99.

EXAMPLE 3

1-(4-amino-6,7-dimethoxy-2-quinazolinyl)-3-(1,1-dimethyl-ethylamino)carbonyl -[(tetrahydro -2-furanyl)carbonyl]-piperazine A solution of (S)-1-(4-Amino-6,7-dimethoxy-2-quinazolinyl)-3-(1,1-dimethylethylamino)carbonyl piperazine (133.2 mg, 0.3429 mmol) was treated with 2-furoyl chloride in dry 1.0 mL THF (14 h). The reaction mixture was concentrated in vacuo and submitted to PCTLC ($SiO_2$, 2 mm, 0–10% $CH_3OH/CH_2Cl_2$) providing the desired amide.

$^1$H NMR ($CDCl_3$, 300 MHz) δ 7.53 (br s, 1H), 7.15 (br s, 1H), 6.89 (br s, 1H), 6.83 (br s, 1H), 6.68 (br s, 1H), 6.52 (d, 1H, J=1.7 Hz), 5.30 (br s, 2H), 5.10–5.23 (br m, 2H), 4.62 (br d, 4H), 4.50 (br d, 1H), 3.97 (s, 3H), 3.94 (s, 3H), 3.18–3.50 (br m, 3H), 1.25 (s, 9H).

FABLRMS 483 ($M^+$+H, $C_{24}H_{30}N_6O_5$ requires 482.5439)

HPLC (Vydac; C18; diameter=4.6 mm; length=15 cm; gradient=$CH_3CN$ [0.1% TFA]-$H_2O$ [0.1% TFA], 5%–95%, 95–5% over 20 min. 1.5 ml/min flow rate; RT=6.57 min; focus=214 nm; 99.4% pure.

Anal. Calcd for $C_{24}H_{30}N_6O_5$ and 0.7 $CH_3OH$ and 0.55 $CH_2Cl_2$: C=54.97, H=6.19, N=15.23. Found: C=54.96, H=5.92, N=15.07.

EXAMPLE 4

(R)-1-(4-Amino-6,7-dimethoxy-2-quinazolinyl)-4-[(1,1-dimethylethoxy) carbonyl]-3-(1,1-dimethylethylamino)carbonyl piperazine A solution of 4-amino-2-chloro-6,7-dimethoxyquinazoline (94.4 mg, 0.3939 mmol) and (R)-4-

[(1,1-dimethylethoxy)carbonyl]-3-(1,1-dimethylethylamino) carbonyl piperazine (see Askin, D. et al., Tetrahedron Letters 1994, 35, 673–676) (112.4 mg, 0.3939 mol) in 2-propanol (1 mL) was heated at 90° C. (24 h). The solvent was removed in vacuo and the residue subjected to PCTLC (SiO$_2$, 2 mm, 0–10% MeOH/CH$_2$Cl$_2$) which afforded ((R)-1-(4-Amino-6,7-dimethoxy-2-quinazolinyl)-4-[(1,1-dimethylethoxy)carbonyl]-3-(1,1-dimethylethylamino)carbonyl piperazine.

$^1$H NMR (CD$_3$OD, 300 MHz) δ 7.37 (br s, 1H), 6.95 (br s, 1H), 5.10 (br s, 1H), 4.63 (br s, 1H), 4.20–4.50 (br m, 2H), 3.92 (s, 3H), 3.89 (s, 3H), 3.60 (br m, 1H), 3.10–3.25 (obscured by CD$_3$OD, 2H), 1.47 (s, 9H), 1.30 (s, 9H).

FABLRMS 489 (M$^+$+H, C$_{24}$H$_{36}$N$_6$O$_5$ requires 488.59172)

HPLC (Vydac; C18; diameter=4.6 mm; length=15 cm; gradient=CH$_3$CN [0.1% TFA]-H$_2$O [0.1% TFA], 5%–95%, 95–5% over 20 min, 1.5 ml/min flow rate; RT=8.42 min; focus=214 nm; 97.3% pure.

Anal. Calcd for C$_{24}$H$_{36}$N$_6$O$_5$ and 0.8 IPA and 1.7 CHCl$_3$: C=45.63, H=6.01, N=11.36. Found: C=45.81, H=5.60, N=11.12.

EXAMPLE 5

(S)-1-(4-Amino-6,7-dimethoxy-2-quinazolinyl)-2-carboxymethyl pyrrolidine and (S)-1-(4-Amino-6,7-dimethoxy-2-quinazolinyl)-2-carboxyisopropyl pyrrolidine A solution of 4-amino-2-chloro-6,7-dimethoxyquinazoline (92.8 mg, 0.387 mmol), diisopropylethyl amine (50 mg, 0.387), and (S)-proline methyl ester (50.0 mg, 0.387 mol) in 2-propanol (1 mL) was heated at 90° C. (24 h). The solvent was removed in vacuo and the residue subjected to preparative HPLC Water Delta Prep 4000 (C18, isocratic 50% CH$_3$CN [0.1% TFA]-50% H$_2$O [0.1% TFA]) to afford (S)-1-(4-Amino-6,7-dimethoxy-2-quinazolinyl)-2-carboxymethyl pyrrolidine and (S)-1-(4-Amino-6,7-dimethoxy-2-quinazolinyl)-2-carboxyisopropyl pyrrolidine. For (S)-1-(4-Amino-6,7-dimethoxy-2-quinazolinyl)-2-carboxymethyl pyrrolidine:

$^1$H NMR (CD$_3$OD, 300 MHz) δ 7.55 (br s, 1H), 7.12 (br s, 1H), 4.85 (m, 1H), 3.98 (s, 3H), 3.92 (s, 3H), 3.77 (s, 3H), 3.72 (obscured by CH3, 2H), 2.39 (br m, 1H), 2.18 (br s, 3H).

FABLRMS 333 (M$^+$+H, C$_{16}$H$_{20}$N$_4$O$_4$ requires 332.36)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=5.69 min; focus=214 nm; 96% pure.

Anal. Calcd for C$_{16}$H$_{20}$N$_4$O$_4$, 0.25 C$_2$HO$_2$F$_3$, and 0.85 H2O: C=45.33, H=4.72, N=11.43. Found: C=45.32, H=4.49, N =11.73.

For (S)-1-(4-Amino-6,7-dimethoxy-2-quinazolinyl)-2-carboxyisopropyl pyrrolidine:

$^1$H NMR (CD$_3$OD, 300 MHz) δ 7.56 (br s, 1H), 7.13 (br s, 1H), 5.04 (m, 1H), 4.80 (m, 1H), 3.98 (s, 3H), 3.92 (s, 3H), 3.73 (br m, 2H), 2.39 (br m, 1H), 2.18 (br s, 3H), 1.29 (d, 1H, J=6.1 Hz), 1.20 (d, 1H, J=6.1 Hz).

FABLRMS 361 (M$^+$+H, C$_{18}$H$_{24}$N$_4$O$_4$ requires 360.42)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=7.09 min; focus=214 nm; 100% pure.

Anal. Calcd for C$_{18}$H$_{24}$N$_4$O$_4$, 1.9 C$_2$HO$_2$F$_3$, and 0.3 H$_2$O: C=44.95, H=4.59, N=9.62. Found: C=44.95, H=4.51, N=9.84.

EXAMPLE 6

(R)-1-(4-Amino-6,7-dimethoxy-2-quinazolinyl)-3-(1,1-dimethylethylamino)carbonyl piperazine A solution of 4-amino-2-chloro-6,7-dimethoxyquinazoline (3.40 g, 14.19 mmol), diisopropylethyl amine (1.84 g, 14.19) and (S)-3-(1,1-dimethylethylamino) carbonyl piperazine (see Askin, D. et al., Tetrahedron Letters 1994, 35, 673–676) (2.63 g, 14.19 mol) in 2-propanol (15 mL) was heated at 90° C. (24 h). The white precipitate was filtered off and washed with cold 2-propanol affording (R)-1-(4-Amino- 6,7-dimethoxy-2-quinazolinyl)-4-[(benzyloxy)carbonyl]-3-(1,1-dimethylethylamino)carbonyl piperazine.

$^1$H NMR (DMSO-d$_6$, 300 MHz) δ 7.41 (s, 1H), 7.25 (s, 1H), 7.11 (br s, 2H), 6.73 (s, 1H), 4.65 (dd, 1H, J=2.4, 12.2 Hz), 4.41 (br d, 1H, J=12.2 Hz), 3.83 (s, 3H), 3.78 (s, 3H), 3.08 (dd, 1H, J=3.1, 10.4 Hz), 2.92 (br d, 1H, J=11.9), 2.50–2.85 (br m, 4H), 1.28 (s, 9H).

FABLRMS 389 (M$^+$+H, C$_{19}$H$_{28}$N$_6$O$_3$ requires 388.47)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=4.58 min; focus=214 nm; 99.4% pure.

Anal. Calcd for C$_{19}$H$_{28}$N$_6$O$_3$ and 0.25 CH$_2$Cl$_2$: C=56.43, H=7.01, N=20.51. Found: C=56.46, H=6.91, N=20.35.

EXAMPLE 7

4-(4-amino-6,7-dimethoxyquinazolin-2-yl)-1-(4-oxo-4H-chromene-2-carbonyl)-piperazine-2-carboxylic acid tert-butylamide (6)

A solution of 3a (105 mg, 0.27 mmol), 5 (56 mg, 0.29 mmol), EDCI (59 mg, 0.31 mmol), and HBT (42 mg, 0.31 mmol) in DMF (1 mL) was treated with diisopropylethylamine (87 mg, 0.67 mmol) at room temperature (24 h). The solvent was removed in vacuo and the residue dissolved in EtOAc, washed with saturated NaHCO$_3$, H$_2$O, and brine, dried (Na$_2$SO$_4$) and concentrated in vacuo. PCTLC (SiO$_2$, 4 mm, 10% EtOH; 90% CH$_2$Cl$_2$) afforded the title compound 6 as a yellow powder.

$^1$H NMR (DMSO, 400 MHz) δ 8.22 (ddd, 1H, J=6.5 Hz), 7.73 (m, 1H), 7.54 (d, 1H, J=8.4 Hz), 7.46 (dd, 1H, J=9.7, 7.4 Hz), 7.10 and 6.73 (two singlets, 1H), 6.87 (d, 1H, J=6.1 Hz), 6.83 (s, 1H), 6.81 and 6.67 (two singlets, 1H), 5.28 (m, 3H), 4.91 and 4.72 (two doublets, 1H, J=13.8 Hz), 4.50 (m, 1H), 3.97 (s, 3H), 3.95 (s, 3H), 3.80 (d, 1H, J=11.6 Hz), 3.40 (m, 2H), 3.13 (m, 1H), 2.93 (m, 1H), 2.09 (s, 1H), 1.26 and 1.17 (two singlets, 9H).

FABLRMS m/e 561 g/mole (M$^+$+H, C$_{29}$H$_{32}$N$_6$O$_6$=561 g/mole.)

HPLC (Vydac; C18; diameter=4.6 mm; length=150 mm; gradient=H$_2$O [0.1% H$_3$PO$_4$]-CH$_3$CN, 95%–5%, 5%–95%, over 16 minutes, 2 ml/min flow rate) RT=7.349 min; focus= 215 nm; 99.5% pure.

Anal. Calcd for C$_{29}$H$_{32}$N$_6$O$_6$•0.45 CH$_2$Cl$_2$: C=59.06, H=5.54, N=14.04. Found: C=59.37, H=5.42, N=13.65.

EXAMPLE 8

As a specific embodiment of an oral composition, 100 mg of the compound of Example 7 is formulated with sufficient finely divided lactose to provide a total amount of 580 to 590 mg to fill a size O hard gel capsule.

EXAMPLE 9

Screening assay: Alpha 1b Adrenergic Receptor Binding

Membranes prepared from the stably transfected human alpha 1b cell line (ATCC CRL 11139) were used to identify compounds that bind to the human alpha 1b adrenergic receptor. These competition binding reactions (total volume=200 µl) contained 50 mM Tris-HCl pH 7.4, 5 mM EDTA, 150 mM NaCl, 100 pM [$^{125}$I]-HEAT, membranes prepared from the alpha 1b cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values <7 nM.

EXAMPLE 10
Selective Binding assays

Membranes prepared from stably transfected human alpha 1d and alpha 1a cell lines (ATCC CRL 11138 and CRL 11140, respectively) were used to identify compounds that selectively bind to the human alpha 1b adrenergic receptor. These competition binding reactions (total volume=200 µl) contained 50 mM Tris-HCl pH 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to bind to the human alpha 1b adrenergic receptor with binding affinities greater than twenty-fold higher than the binding affinities with which they bind to the human alpha 1 d and alpha 1a adrenergic receptors.

EXAMPLE 11

EXEMPLARY COUNTERSCREENS
1. Assay Title: Dopamine $D_2$, $D_3$, $D_4$ in vitro screen
Objective of the Assay The objective of this assay is to eliminate agents which specifically affect binding of [3H] spiperone to cells expressing human dopamine receptors $D_2$, $D_3$ or $D_4$.
Method Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.
2. Assay Title: Serotonin 5HT1a
Objective of the Assay The objective of this assay is to eliminate agents which specifically affect binding to cloned human 5HT1a receptor.
Method Modified from Schelegel and Peroutka *Biochemical Pharmacology* 35: 1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM $CaCl_2$ and 1 mg/ml ascorbate. Non-specific binding is defined using 10 µM propranolol. The assay is terminated after a 1 hour incubation at room temperature by rapid filtration over GF/C filters

EXAMPLE 12

EXEMPLARY FUNCTIONAL ASSAYS

In order to confirm the specificity of compounds for the human alpha 1b adrenergic receptor and to define the biological activity of the compounds, the following functional tests may be performed:
1. In vitro Rat, Dog and Human Prostate and Dog Urethra Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (−log $K_b$) values were obtained from Schild plot when three or more concentrations were tested. When less than three concentrations of antagonist are tested, $K_b$ values are calculated according to the following formula $$K_b = \frac{[B]}{x-1},$$

where x is the ratio of $EC_{50}$ of agonist in the presence and absence of antagonist and [B] is the antagonist concentration.
2. Measurement of Intra-Urethral Pressure in Anesthetized Dogs

PURPOSE

Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because the alpha 1a receptor subtype has been identified as the predominent subtype in the human prostate, it is now possible to specifically target this receptor to inhibit prostatic contraction without concomitant changes in the vasculature. Alternatively, since it is now believed that the alpha 1b receptor subtype is predominantly responsible for mediating changes in the vasculature, it is now possible to specifically target the alpha 1b receptor subtype to lower arterial pressure without concomitant changes in urethral pressure. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS

Male mongrel dogs (7–12 kg) are used in this study.

The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing arterial pressure is also present in urethral smooth muscle. According to this method, one is able to confirm the selectivity of alpha 1b adrenergic receptor antagonists that prevent the increase in arterial pressure to phenylephrine without any activity in inter-urethral pressure.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula

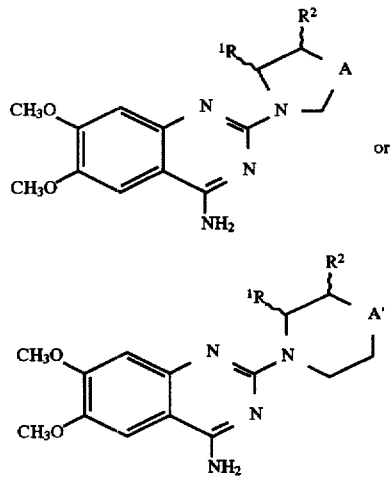

wherein

A is selected from $CR^3R^8$, $N-R^3$, O, S or $SO_2$;

A' is selected from $CR^3R^8$ or $N-R^3$.

$R^1$ and $R^2$ are each independently selected from hydrogen, CN, $C(O)R^4$, $CH_2OR^4$, $CH_2NR^4R^5$, $CONR^4R^5$, $CO_2R^4$ or $SO_2R^4$, provided that $R^1$ and $R^2$ are not both hydrogen;

$R^3$ is selected from hydrogen, CN, $OR^6$, $NR^6R^7$, $C(O)R^4$, $CO_2R^4$, $CONR^4R^5$, Het or $(CH_2)_m Ar$ where Ar is unsubstituted, mono-, di- or tri-substituted Ar and where the substituents on Ar are independently selected from $OR^4$, $NR^4R^5$, halogen, $C_{1-8}$ alkyl, $CF_3$, nitro or CN;

$R^4$ and $R^5$ are each independently selected from hydrogen, $CH_2CF_3$, $C_{1-8}$ alkyl, $C_{3-8}$ cycloalkyl, Het or $(CH_2)_m Ar$, where Ar is unsubstituted, mono-, di- or tri-substituted Ar and where the substituents on Ar are independently selected from $OR^6$, halogen, $NR^6R^7$, $C_{1-8}$ alkyl, $CF_3$ or $C_{3-8}$ cycloalkyl;

$R^6$ and $R^7$ are each independently selected from hydrogen, $CH_2CF_3$, $C_{1-8}$ alkyl or $C_{3-8}$ cycloalkyl;

$R^8$ is selected from hydrogen, $C_{1-8}$ alkyl, $CF_3$, $C_{3-8}$ cycloalkyl, Het or $(CH_2)_m Ar$ where Ar is unsubstituted, mono-, di- or tri-substituted Ar and where the substituents on Ar are independently selected from $OR^4$, $NR^4R^5$, halogen, $C_{1-8}$ alkyl, $CF_3$, nitro or CN;

Ar is selected from phenyl, naphthyl, furanyl, thiazolyl, pyrrolyl, thienyl, 2-, 3-or 4-pyridyl, or chromanyl;

Het is an unsubstituted, mono- or di-substituted heterocyclic ring selected from tetrahydrofuranyl, pyrrolidinyl, piperidinyl, piperazinyl or morpholinyl, where the substituents on Het are independently selected from hydroxyl, $C_{1-8}$ alkyl, $CF_3$, halogen, CN, nitro, $C_{1-4}$ alkoxy, amino or $CO_2$-$C_{1-4}$ alkyl;

m is an integer from zero to three;

and the pharmaceutically acceptable salts thereof.

2. The compound of claim 1 selected from

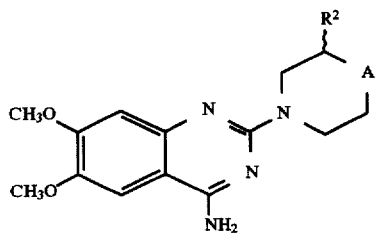

or

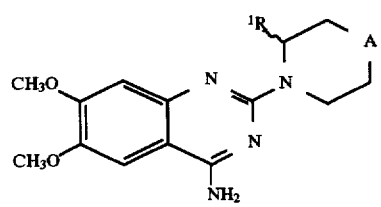

wherein $R^1$ and $R^2$ are each independently selected from CN, $C(O)R^4$, $CH_2OR^4$, $CH_2NR^4R^5$, $CONR^4R^5$, $CO_2R^4$ or $SO_2R^4$;

$R^4$ is selected from hydrogen, $CH_2CF_3$, $C_{1-6}$ alkyl, $C_{3-6}$ cycloalkyl, Het or $(CH_2)_m Ar$ where Ar is unsubstituted, mono-, di- or tri-substituted Ar and the substituents on Ar are independently selected from $OR^6$, halogen, $NR^6R^7$, $C_{1-5}$ alkyl, $CF_3$ or $C_{3-8}$ cycloalkyl; and $R^5$ is selected from hydrogen, $CH_2CF_3$, $C_{1-8}$ alkyl or $C_{3-8}$ cycloalkyl;

and the pharmaceutically acceptable salts thereof.

3. The compound of claim 2, wherein A is selected from $CR^3R^8$ or $N-R^3$;

$R^1$ and $R^2$ are each independently selected from CN, $CONR^4R^5$ or $CO_2R^4$;

$R^3$ is selected from hydrogen, $C(O)R^4$ or $CO_2R^4$;

$R^4$ is selected from $C_{1-6}$ alkyl, $C_{3-6}$ cycloalkyl, tetrahydrofuranyl or $(CH_2)_m Ar$ where Ar is unsubstituted, mono-, di- or tri-substituted Ar and the substituents on Ar are independently selected from $OR^6$, halogen, $C_{1-4}$ alkyl or $C_{3-8}$ cycloalkyl;

$R^5$ is selected from hydrogen, $C_{1-6}$ alkyl or $C_{3-6}$ cycloalkyl;

Ar is selected from phenyl, furanyl or chromanyl; and m is an integer of from zero to two;

and the pharmaceutically acceptable salts thereof.

4. The compound of claim 2, of the formula

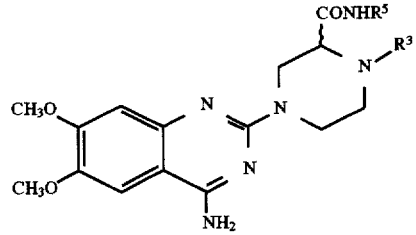

wherein $R^4$ is selected from $C_{1-4}$ alkyl, benzyl, furanyl, tetrahydrofuranyl or 4-oxo-chromene; and $R^5$ is selected from hydrogen, $C_{1-4}$ alkyl or $C_{3-6}$ cycloalkyl;

and the pharmaceutically acceptable salts thereof.

5. The compound of claim 4, of the formula

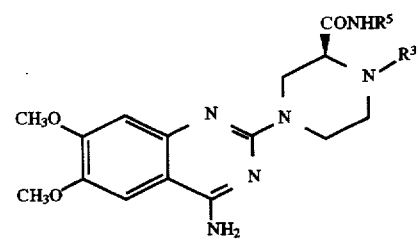

and the pharmaceutically acceptable salts thereof.

6. The compound of claim 5, of the formula

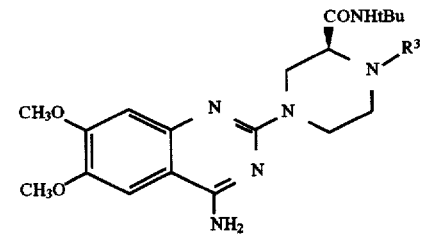

and the pharmaceutically acceptable salts thereof.

7. The compound of claim 4, selected from (S)-1-(4-Amino-6,7-dimethoxy-2-quinazolinyl)-4-[(benzyloxy)carbonyl]-3-(1,1-dimethylethylamino) carbonyl piperazine;

(S)-1-(4-Amino-6,7-dimethoxy-2-quinazolinyl)-3-(1,1-dimethylethylamino)carbonyl piperazine;

1-(4-amino-6,7-dimethoxy-2-quinazolinyl)-3-(1,1-dimethylethylamino)carbonyl -[(tetrahydro-2-furanyl)carbonyl]-piperazine;

(R)-1-(4-Amino-6,7-dimethoxy-2-quinazolinyl)-4-[(1,1-dimethylethoxy)carbonyl]-3-(1,1-dimethylethylamino) carbonyl piperazine;

(R)-1-(4-Amino-6,7-dimethoxy-2-quinazolinyl)-3-(1,1-dimethylethylamino)carbonyl piperazine; or 4-(4-amino-6,7-dimethoxyquinazolin-2-yl)-1-(4-oxo-4H-chromene-2-carbonyl)-piperazine-2-carboxylic acid tert-butylamide;

and the pharmaceutically acceptable salts thereof.

8. The compound of claim 2, of the formula

[structure with CH₃O groups on benzene ring, CONR⁴R⁵ group, A, NH₂]

and the pharmaceutically acceptable salts thereof.

9. The compound of claim 8 wherein

A is selected from CR³R⁸ or N—R³;

and the pharmaceutically acceptable salts thereof.

10. The compound of claim 9, of the formula

[structure with CH₃O groups, CONR⁴R⁵, R³, NH₂]

wherein

R³ is selected from hydrogen, C(O)R⁴ or CO₂R⁴;

Ar is selected from phenyl, furanyl or chromanyl; and

Het is tetrahydrofuranyl;

and the pharmaceutically acceptable salts thereof.

11. The compound of claim 10, of the formula

[structure with CH₃O groups, CONHR⁵, R³, NH₂]

wherein

R⁵ is selected from hydrogen, $C_{1-6}$ alkyl or $C_{3-6}$ cycloalkyl;

and the pharmaceutically acceptable salts thereof.

12. The compound of claim 11, of the formula

[structure with CH₃O groups, CONHR⁵, R³, NH₂]

wherein

R⁴ is selected from $C_{1-4}$ alkyl, benzyl, furanyl, tetrahydrofuranyl or 4-oxo-chromene; and R⁵ is $C_{1-4}$ alkyl;

and the pharmaceutically acceptable salts thereof.

13. A pharmaceutical composition comprising a therapeutically effective amount of the compound of claim 1 and a pharmaceutically acceptable carrier.

14. A method of treating hypertension in a subject in need thereof which comprises administering to the subject a therapeutically effective amount of the compound of claim 1.

15. A method of treating hypertension in a subject in need thereof which comprises administering a therapeutically effective amount of the composition of claim 13.

16. A method of treating a disease which is susceptible to treatment by selective antagonism of the alpha 1b receptor which comprises administering to a subject in need thereof an amount of the compound of claim 1 effective to treat the disease.

17. A drug which is useful for treating hypertension in a mammal in need thereof, the effective ingredient of the said drug being the compound of claim 1.

* * * * *